United States Patent
Ho et al.

(10) Patent No.: US 10,548,720 B2
(45) Date of Patent: Feb. 4, 2020

(54) METHODS AND APPARATUS FOR TREATING GLOTTIC INSUFFICIENCY

(71) Applicant: APREVENT MEDICAL INC., Taipei (TW)

(72) Inventors: Guan-Min Ho, Taipei (TW); Yenyu Chen, Taipei (TW); Chia-Yuan Chang, Taipei (TW)

(73) Assignee: APREVENT MEDICAL INC. (KY)

( * ) Notice: Subject to any disclaimer, the term of this patent is extended or adjusted under 35 U.S.C. 154(b) by 204 days.

(21) Appl. No.: 15/586,294

(22) Filed: May 4, 2017

(65) Prior Publication Data

US 2017/0231754 A1    Aug. 17, 2017

Related U.S. Application Data

(63) Continuation of application No. 15/310,107, filed as application No. PCT/US2015/020633 on Mar. 15, 2015, now Pat. No. 9,675,447.

(60) Provisional application No. 62/065,457, filed on Oct. 17, 2014, provisional application No. 62/048,816, filed on Sep. 11, 2014.

(51) Int. Cl.
  *A61F 2/20*   (2006.01)
  *A61M 25/10*  (2013.01)

(52) U.S. Cl.
  CPC ............ *A61F 2/20* (2013.01); *A61M 25/1002* (2013.01); *A61F 2002/206* (2013.01); *A61F 2250/0003* (2013.01); *A61F 2250/0012* (2013.01); *A61F 2250/0075* (2013.01)

(58) Field of Classification Search
  CPC ..... A61F 2002/206; A61F 2/20; A61M 25/10; A61M 5/00; A61M 29/02; A61M 16/00; A61B 19/00

USPC ............................................. 623/9
See application file for complete search history.

(56) References Cited

U.S. PATENT DOCUMENTS

| | | | |
|---|---|---|---|
| 4,846,174 A | * | 7/1989 | Willard .......... A61M 25/09041 606/194 |
| 5,197,982 A | | 3/1993 | Goldsmith, III et al. |
| 5,201,765 A | | 4/1993 | Netterville et al. |
| 5,306,298 A | | 4/1994 | Godley, III et al. |
| 5,326,375 A | | 7/1994 | Montgomery et al. |
| 2004/0030347 A1 | | 2/2004 | Gannoe et al. |
| 2010/0023125 A1 | | 1/2010 | Debry et al. |

(Continued)

FOREIGN PATENT DOCUMENTS

| JP | 2008073206 A | 4/2008 |
|---|---|---|
| JP | 2009006090 A | 1/2009 |
| WO | 2014145327 A1 | 9/2014 |

OTHER PUBLICATIONS

Shinobu Jwamura et al., "A Newer Arytenoid Adduction Technique for One-Vocal-Fold Paralysis—A Direct Pull of the Lateral Cricoarytenoid Muscle", Head and Neck Surgery, 1996, pp. 1-10, vol. 6, No. 1.

(Continued)

*Primary Examiner* — Yashita Sharma
(74) *Attorney, Agent, or Firm* — SU IP Consulting

(57) ABSTRACT

An implant system for treating glottic insufficiency includes an implant, which includes a balloon with a port connector or a catheter and a band comprising a proximate end attached to a portion of the balloon that translates away from the port connector or the catheter when the balloon is inflated through the port connector or the catheter.

13 Claims, 9 Drawing Sheets

(56) References Cited

U.S. PATENT DOCUMENTS

| | | |
|---|---|---|
| 2011/0301580 A1 | 12/2011 | Hoffman |
| 2012/0150293 A1 | 6/2012 | Hoffman et al. |
| 2013/0281973 A1 | 10/2013 | McCulloch et al. |
| 2014/0128664 A1 | 5/2014 | Ogdahl et al. |
| 2017/0056160 A1 | 3/2017 | Ho et al. |

OTHER PUBLICATIONS

Md Peak Woo, "Arytenoid Adduction and Medialization Laryngoplasty", Otolayngologic Clinics of North America, Aug. 2000, pp. 817-839, vol. 33, No. 4.

International Search Report and Written Opinion of the International Searching Authority, International application No. PCT/US2015/020633, dated Jun. 17, 2015.

The Extended European Search Report, Application No. 15840169.5, dated Apr. 16, 2018.

\* cited by examiner

METHODS AND APPARATUS FOR TREATING GLOTTIC INSUFFICIENCY

CROSS-REFERENCE TO RELATED APPLICATIONS

The present application is a continuation under 35 U.S.C. § 120 of U.S. Nonprovisional application Ser. No. 15/310,107, filed Nov. 10, 2016, which is a U.S. National Stage filing under 35 U.S.C. § 371 of International Application PCT/US2015/020633, filed Mar. 15, 2015, which claims the benefit of U.S. Provisional Application No. 62/048,816, filed Sep. 11, 2014, and U.S. Provisional Application No. 62/065,457, filed Oct. 17, 2014. The U.S. Nonprovisional Application, the International Application, and the U.S. Provisional Applications, including any appendices or attachments thereof, are incorporated by reference herein in their entirety.

BACKGROUND

Dysphagia associated with aspiration pneumonia often occurs in patients with neurological disorders. The neurological disorders may be caused by stroke, brain surgery, head and/or spinal cord trauma, oropharyngeal disease, radiation therapy, cardiac/thoracic surgery, autoimmune or other degenerative neurologic diseases. The aspiration pneumonia may be mainly caused by glottic insufficiency, due to vocal fold paralysis with/without swallowing dysfunction. Stroke patients with aspiration symptoms may have a seven-time higher risk in developing aspiration pneumonia than other types of patients. For these stroke patients, even after recovery, there is still a relatively high incidence of dysphagia associated with aspiration pneumonia.

Conventional surgical techniques to treat dysphagia and glottic insufficiency may include Type I Medialization Thyroplasty (MT) procedure and Arytenoid Adduction (AA) procedure. Type I MT procedure is the main phonosurgical procedure performed in patients with glottic insufficiency. The primary limitations of Type I MT procedure include the inability to close a wide posterior glottal chink and restore the physiological swallowing steps, like laryngeal elevation and vocal fold movement. For patients with vocal cord paralysis and a significant posterior glottic gap after the Type I MT procedure, an AA procedure may be performed subsequently to close the incompletely closed posterior glottis. Still, one limitation of the AA procedure, associated with the posterior airway closure, is an increased frequency of postoperative airway complaints after the AA procedure, due to postoperative tissue edema in the glottis area. Further, Type I MT and AA procedures may not be suitable for patients having difficulty with prolonged periods of supine positioning or intolerable for long lasting surgical procedures.

Since the above two procedures either use implants or suture fixation technique, a common complaint from these procedures is the inability to precisely adjust the implant or sutures intraoperatively and postoperatively. Specifically, it is difficult to accurately perform intraoperative adjustment of implant due to edematous swelling of vocal tract mucosa caused by these procedures. For example, carving an implant during surgery may result in prolonged operation time and suboptimal shaping of the implant. Furthermore, these implants cannot be postoperatively adjusted at all.

Providing an adjustable implant for the procedure would shorten the operation time, and reduce the risk of postoperative airway compromise. The adjustable implant would be customized for each individual's needs, from which the patient could greatly benefit.

SUMMARY

In examples of the present disclosure, an implant system to treat glottic insufficiency includes an implant with a balloon and a band. The balloon has a port connector, and the band has a proximate end attached to a portion of the balloon that translates away from the port connector when the balloon is inflated through the port connector.

In examples of the present disclosure, a method to treat glottis insufficiency includes creating a window in a thyroid cartilage, inserting the implant through the window and into a paraglottic space, securing the band to a thyroarytenoid muscle complex, including surrounding connective tissue, and inflating the balloon to pull the band, which in turn pulls on the thyroarytenoid muscle complex, which in turn rotates an arytenoids cartilage to medialize and tighten a vocal cord.

DETAILED DESCRIPTION

Figure 1A:
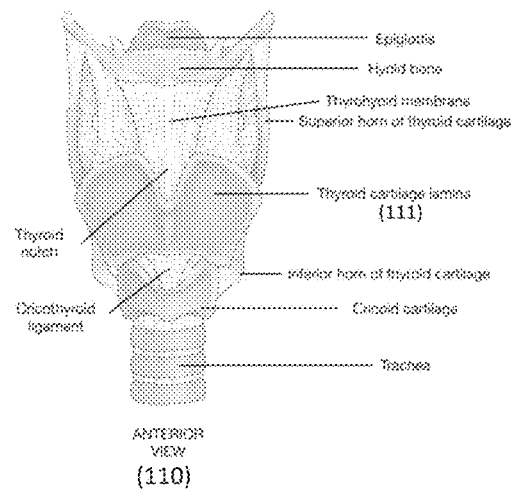
FIG. 1A illustrates various views of larynx anatomy.
Figure 1A:
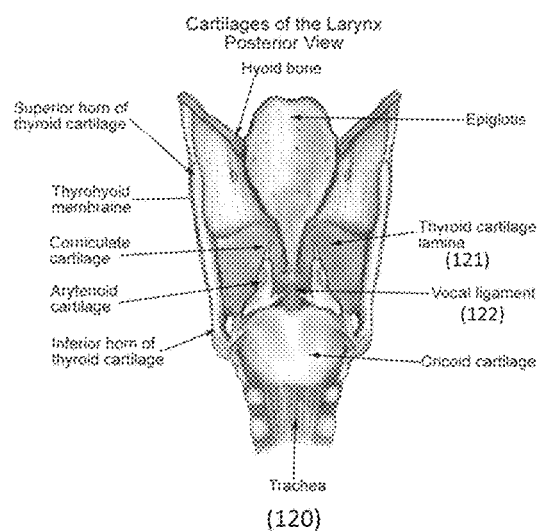
Figure 1A:
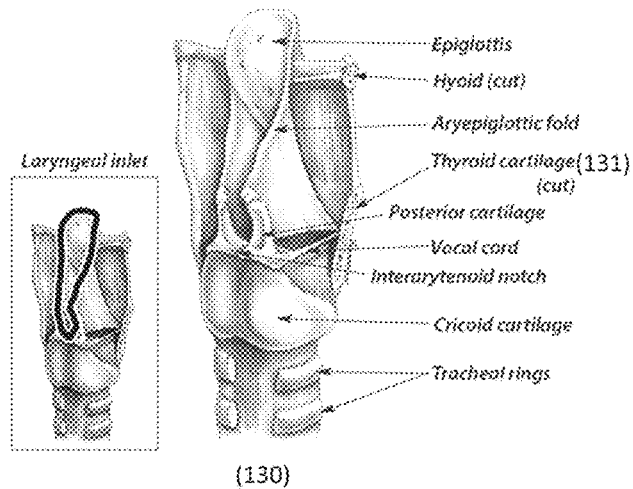

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

The present disclosure describes apparatuses and methods to treat dysphagia, glottic insufficiency (due to neuromuscular incoordination or disordered interaction (cooperation) between the intrinsic muscles), and the poor closure of larynx inlet (opening) (due to uncoordinated bending of epiglottis and delayed or absence of laryngeal elevation). The disclosed treatments may improve the glottic closure, reduce the incidence of aspiration, and thus preventing the aspiration's sequelae, such as aspiration pneumonia. Furthermore, the disclosed treatments may enable the postoperative adjustment of implants, and reduce the risk of postoperative airway compromise. As a result, the disclosed treatments may shorten the operation time during the surgical procedures, and effectively reduce/prevent aspiration pneumonia after the surgical procedures.

In examples of the present disclosure, an implant system mimics the contraction of the thyroarytenoid muscle to close the glottis by rotating the arytenoid cartilage. The contraction is adjustable by changing the size of an implant by changing the amount of filler in the implant. The present disclosure may replace both type I thyroplasty and AA surgical techniques because it offers shortened surgical time and postoperatively adjustable implant size.

FIG. 1A illustrates various views of larynx anatomy.

Drawing 110 shows the anatomy of a patient's larynx in an anterior view, with the outer side 111 of the thyroid cartilage exposed. Drawing 120 shows the same patient's larynx in a posterior view, with the inner side 121 of the thyroid cartilage exposed. Drawing 120 further shows the patient's vocal ligament 122, which are enclosed within the patient's vocal folds (not shown in the drawing 120). Drawing 130 shows the same patient's laryngeal cartilages (including a cross-sectional view 131 of the thyroid cartilage) in an angled lateral view. In examples of the present disclosure, the space surrounded by the laryngeal cartilages, as well as the tissues and organs connected to these cartilages, may be deemed a "paraglottic space." In other words, the paraglottic space may be a space bounded by the thyroid cartilage and the various surrounding membranes.

Figure 1B:
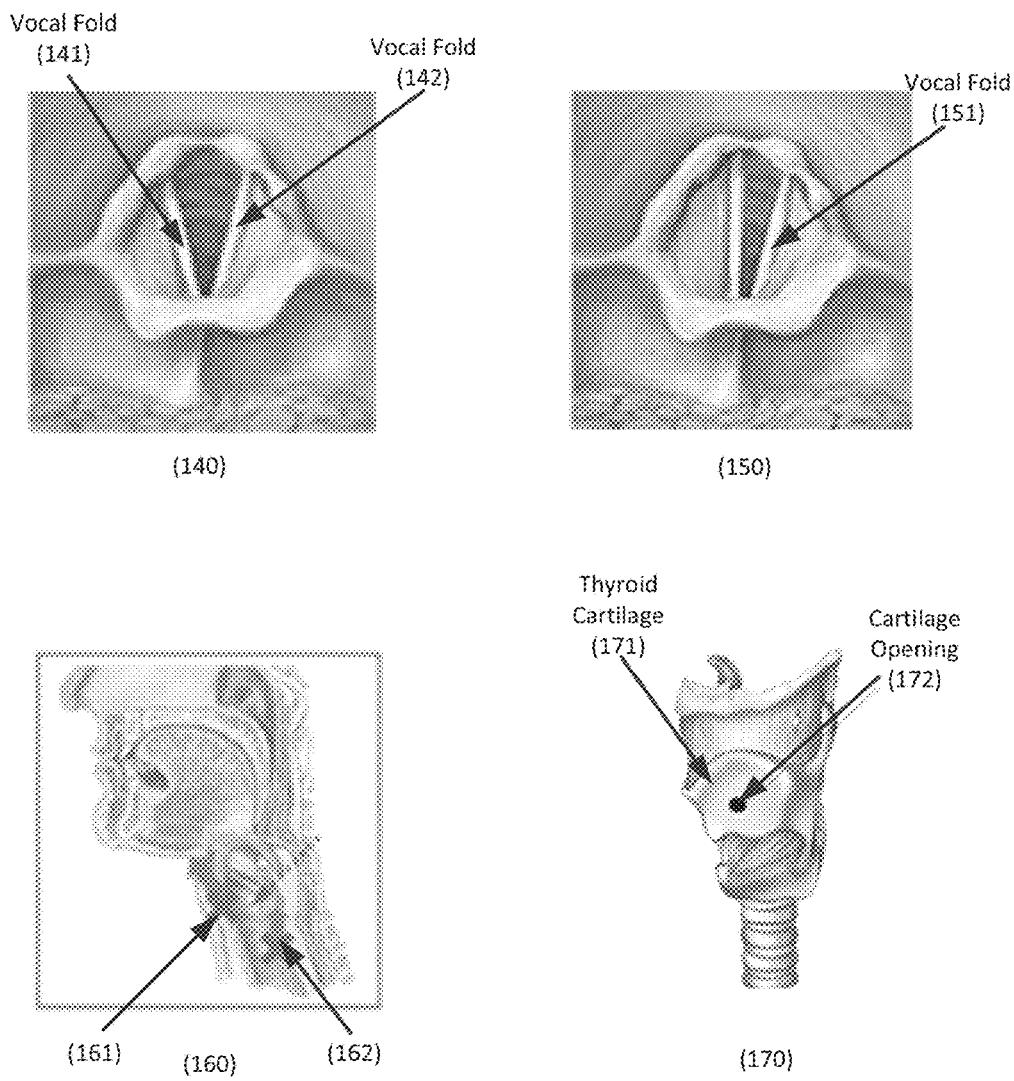
FIG. 1B illustrates various symptoms of glottic insufficiency.

FIG. 1B illustrates various symptoms of glottic insufficiency.

Drawing 140 illustrates an example healthy vocal cord having two lateralized vocal folds 141 and 142. During normal breathing, swallowing or speaking, the two vocal folds 141 and 142 open and close in unison. Before a person swallows food, the food or drink is first crushed and/or mixed into a pasty mass known as a bolus. During swallowing, the person's extrinsic and intrinsic muscles cooperate to prevent food or drink from entering the glottis. For example, the person's extrinsic muscles elevate the larynx and bend the epiglottis over the entrance to the glottis so that the bolus can glide across the epiglottis rather than falling into the larynx. While this movement is under way, the person's intrinsic muscles close the glottis. Should any food particles or liquids touch the surface of the vestibular or vocal folds 141 and 142, a cough reflex may be triggered to prevent the material from entering the glottis.

Drawing 150 illustrates an example unhealthy vocal cord having a paralyzed vocal fold 151 unable to move to a fully lateralized/medialized position. In other words, the paralyzed vocal fold 151 cannot be opened and closed in unison with the other vocal fold, leaving an opening or gap in the glottis. Thus, during swallowing, the bolus may inadvertently slip into the larynx and subsequently into the trachea, bronchus, and lungs, which may lead to infection and pneumonia. Further, as shown in drawing 160, for some of the stroke patients, due to impaired neurological stimulus, the trigger of epiglottis bending, the vocal closure 161, and/or the laryngeal elevation 162 are delayed or absent, leading to incoordination of their extrinsic and intrinsic muscle movements. As a result, the patient may have difficulty swallowing and choking as well.

To treat a patient's glottic insufficiency and/or swallowing difficulty, drawing 170 shows that a surgeon or a medical machinery utilizes a surgical device to create a cartilage opening 172 in the patient's thyroid cartilage 171. The surgical device may perform certain functions such as drilling, shaping, space expansion (e.g., "dissection"), and instrument/implant delivery. Afterwards, the surgeon or the medical machinery places an implant system through the cartilage opening 172 into the paraglottic space behind the patient's thyroid cartilage 171. The implant system is configured to facilitate epiglottis bending or perform laryngeal elevation so that a paralyzed larynx may be better closed during bolus swallowing.

Figure 2A:
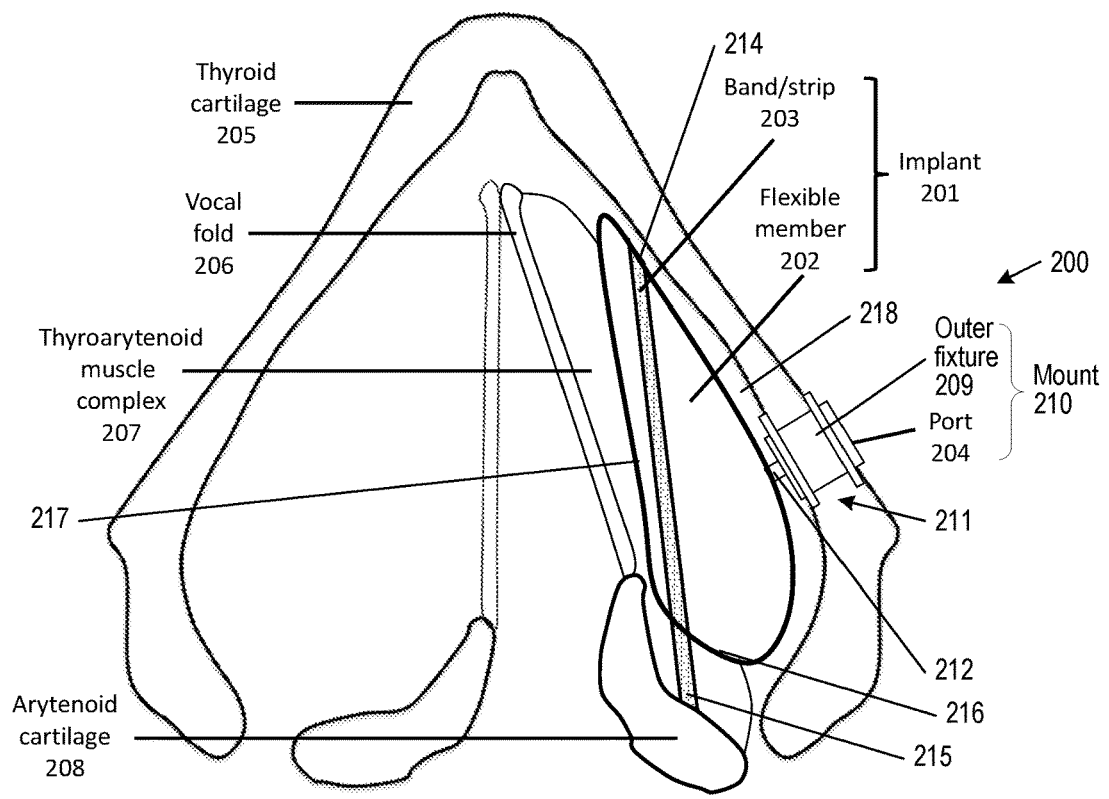
FIGS. 2A and 3 illustrate top and lateral views of an implant system with an implant in a paraglottic space to treat glottic insufficiency and a mount to fix the implant to a thyroid cartilage in examples of the present disclosure.

FIG. 2A illustrates a top view of an implant system 200 positioned in a paraglottic space for treating glottic insufficiency in examples of the present disclosure. The top of the figure is the anterior aspect of larynx and the bottom of the figure is the posterior aspect of larynx. The implant system 200 includes an implant 201. The implant 201 includes at least one main body 202 and at least one band or strip 203. The implant 201 is inserted through an opening or window 211 in the thyroid cartilage 205 into the paraglottic space. The main body 202 has a shape that fits into the paraglottic space between the thyroid cartilage 205, adipose tissue, and the thyroarytenoid muscle complex 207. The main body 202 may be a flexible or expandable member. Inflation of the flexible member 202 may push thyroarytenoid muscle complex 207 and a vocal fold 206 medially and may cause rotation of the arytenoid cartilage 208, which may benefit the glottic closure. The flexible member 202 may be a balloon or another similar device that may expand and contract. For example, the flexible member 202 is substantially a triangular block shaped balloon with a first lateral surface 216 corresponding to the arytenoid cartilage 208, a second lateral surface 217 corresponding to the vocal cord 206, and a third lateral surface 218 corresponding to the thyroid cartilage 205.

The implant system 200 includes a mount 210 secured to the opening 211 in the thyroid cartilage 205. The mount 210 fixes the flexible member 202 to the thyroid cartilage 205.

The implant system 200 includes a port 204. The port 204 is a device configured to maintain and deliver filler. The filler may be added to or removed from the flexible member 202 intraoperatively or postoperatively. In some example, the port 204 is part of the mount 210 that fixes the flexible member 202 to the thyroid cartilage 205. The port 204 fits in an outer fixture 209 of the mount 210. The port 204 is connected to the flexible member 202 via a port connector 212 on the lateral side 218 of the flexible members 202 facing the thyroid cartilage 205. Further device fixation and stabilization can be provided when the outer fixture 209 or the port 204 is nailed or screwed to the thyroid cartilage 205.

In other examples, the port 204 is separate from the mount 210. The port 204 is located away from the mount 210, such as in a lower area of the neck. The port 204 is connected to the flexible member 202 via a catheter on the lateral side 218 of the flexible member 202.

The flexible member 202 and band 203 are made of biocompatible materials, such as silicon or biodegradable materials. The flexible member 202 may be composed with a layer of varied stiffness and/or thickness in order to provide a designated expansion direction.

The band 203 may be rigid, semi-rigid, or soft. It may be made by integrating meshed textile into biocompatible materials. Stiffness of this layer can be changed by the mesh density of the integrated textiles. The band 203 has a proximate end 214 attached to a portion of the flexible member 202 that translates away from the port connector 212 when the flexible member 202 is inflated through the port connector 212. The portion may be part of the superior, inferior, lateral, or medial surface of the expandable member 202.

Figure 2B:
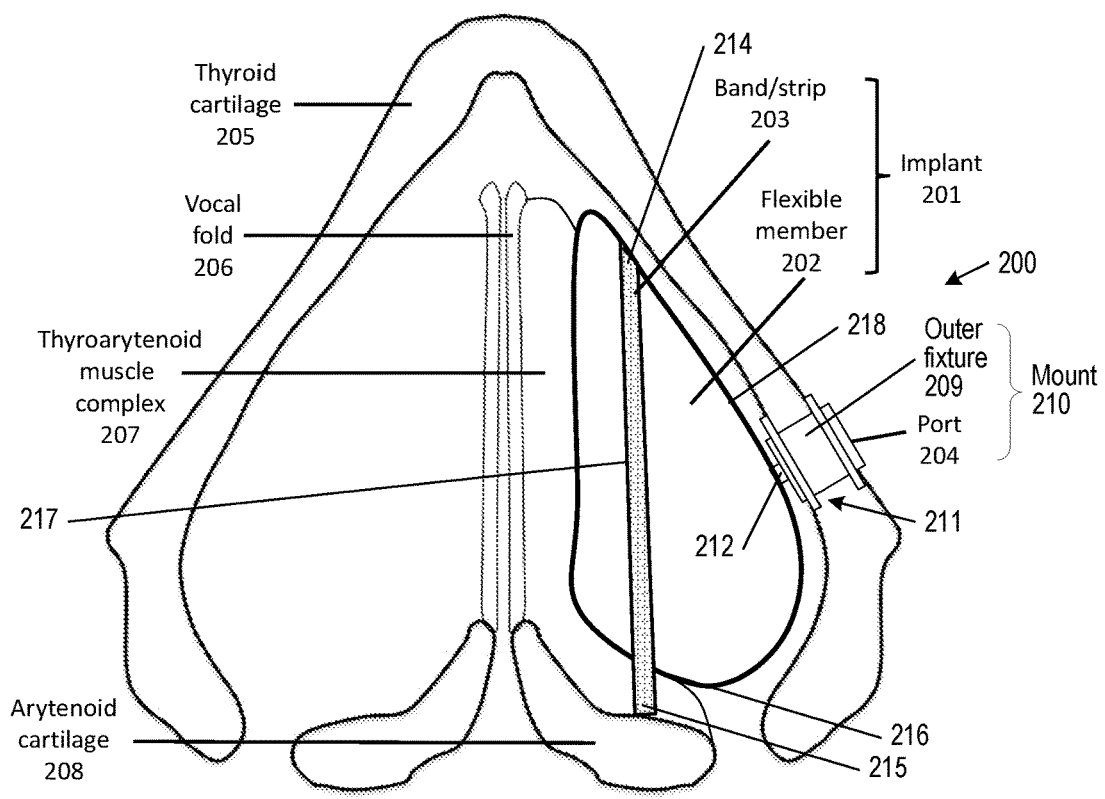
FIGS. 2B and 4 illustrate a mechanism of the implant of FIGS. 2A and 3 in examples of the present disclosure.

FIG. 2B shows therapeutic effects after the implant system 200 is planted into the paraglottic space. The shape and size of the flexible member 202 may be adjustable by adding/removing filler to/from the flexible member 202 via the port 204 during operation (intraoperatively). After operation (postoperatively), when a complication occurs, the flexible member 202 may be readjusted to handle airway compromise. Thus, the implant system 200 may effectively medialize and tighten the paralyzed vocal fold 206. As a result, the risk of aspiration pneumonia can be significantly reduced. The implant system 200 may be similarly adjusted and readjusted either intraoperatively or postoperatively. Thus, the implant system 200 may allow faster operation time, which in turn would increase patients' acceptance of the procedure.

Figure 3:
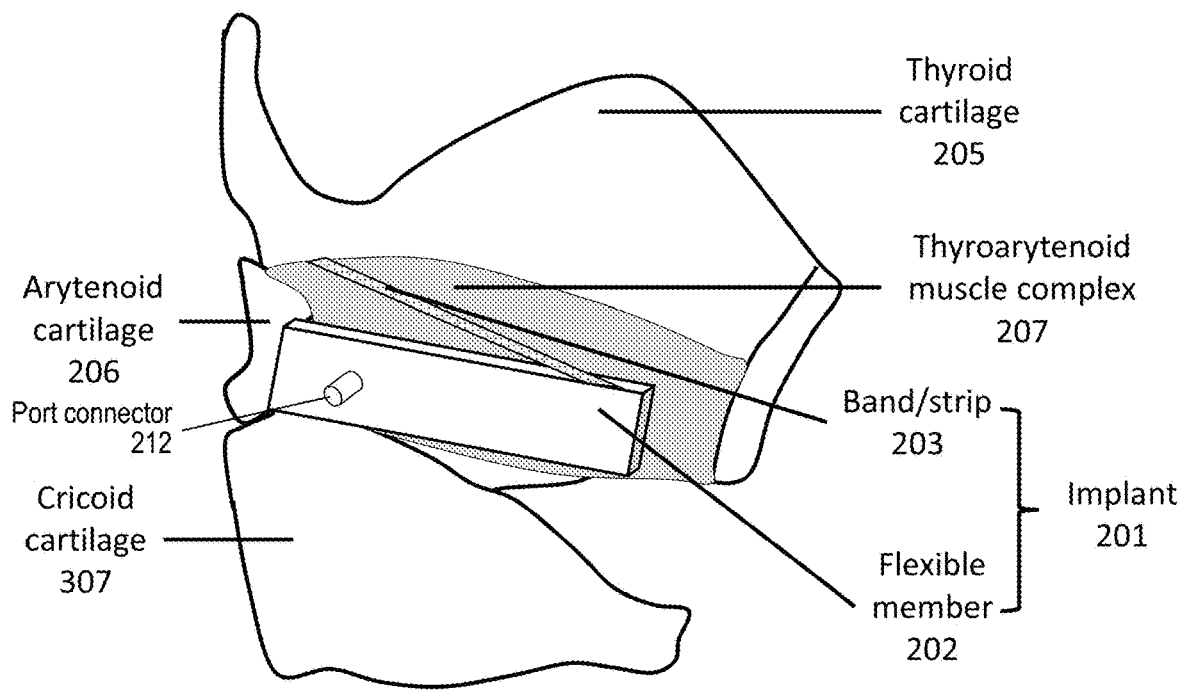

FIG. 3 illustrates a lateral view of the implant system 201 positioned at the paraglottic space for treating glottic insufficiency in examples of the present disclosure. The right-hand side of the figure is the anterior aspect of the larynx and the left-hand side of the figure is the posterior aspect of the larynx. The flexible member 202 is deployed into the space between the thyroid cartilage 205, adipose tissue, and the thyroarytenoid muscle complex 207. A portion of the flexible member 202 indirectly contacts the arytenoid cartilage 208 through muscles and connective tissues therebetween. The proximate end 214 of the band 203 may be integrated into or otherwise attached to the flexible member 202 at its lateral, superior, and/or inferior surfaces while a distal end 215 is attached or otherwise secured to the posterior portion of the thyroarytenoid muscle complex 207 by, e.g., sutures, clips, or hooks.

Expansion of the flexible member 202 may contribute to both medial movement of the paralyzed vocal fold 206 (FIG. 2) and rotation of the arytenoid cartilage 208. The flexible member 202 may also extend its position vertically, thus reaching the supraglottic space, resulting in elevation of larynx and acceleration of epiglottis closure during swallowing. The flexible member 202 may be extended into the para-epiglottic space, to enhance closure of the paralyzed vocal fold 206 to a nearly complete or fully medialized position.

Figure 4:
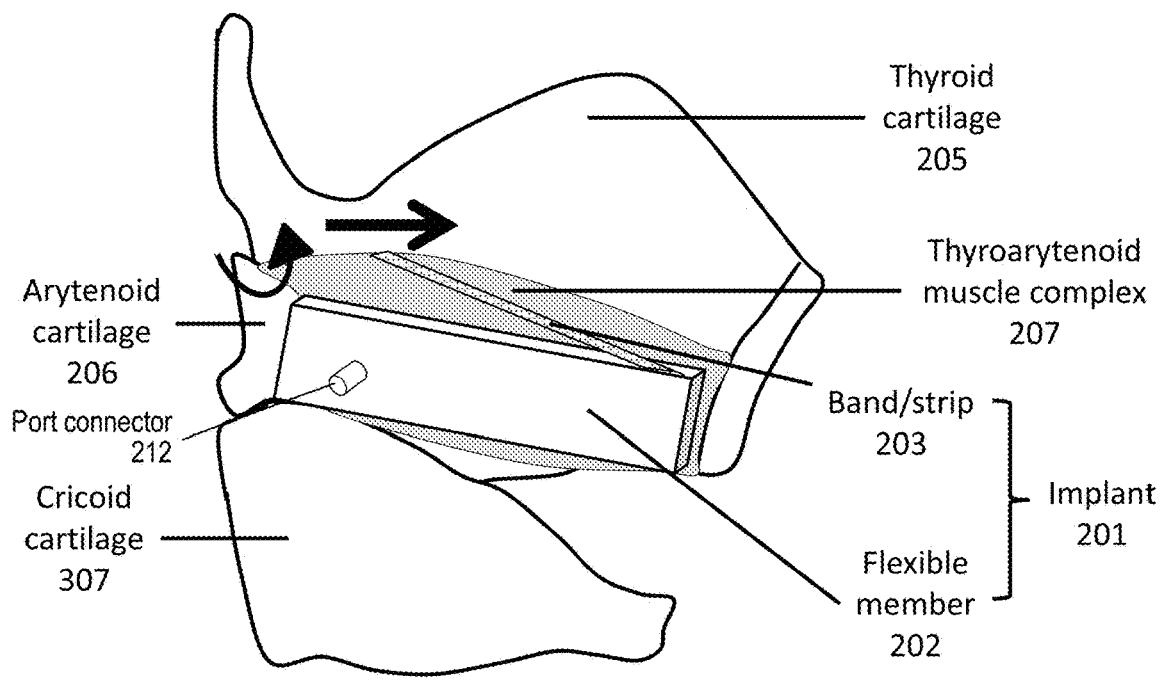

FIGS. 2B and 4 illustrate a mechanism of implant 201 for bringing the paralyzed vocal fold 206 (FIG. 2) to a nearly complete or fully medialized position in examples of the present disclosure. The left-hand side of the figure demonstrates the implant 201 before inflation of the flexible member 202, and the right-hand side of the figure demonstrates the implant 201 after inflation of the flexible member 202. Inflation of the flexible member 202 causes the band 203 to move in a designated direction 402. The movement of the band 203 creates a traction force on the thyroarytenoid muscle complex 207. Traction of the thytoarytenoid muscle complex 207 leads to rotation of the arytenoid cartilage 208. Rotation of the arytenoid cartilage 208 positions the paralyzed vocal fold 206 (FIG. 2) to a nearly complete or fully medialized position.

Figure 5A:
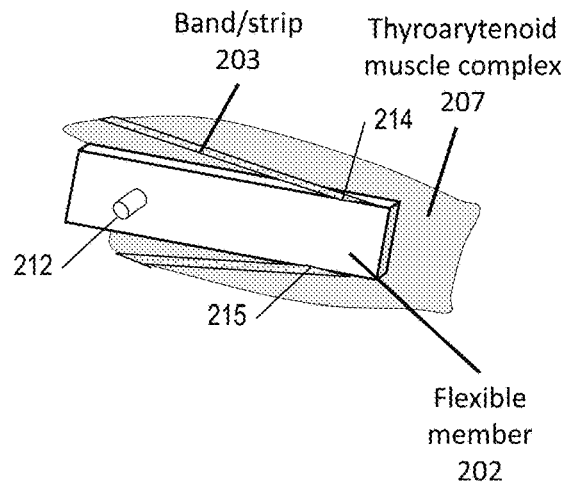
FIGS. 5A, 5B, and 5C illustrate methods of connecting the implant of FIG. 2 with thyroarytenoid muscle in examples of the present disclosure.
Figure 5B:
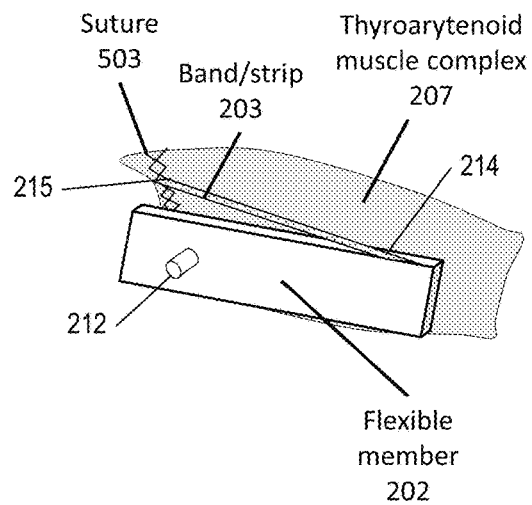
Figure 5C:
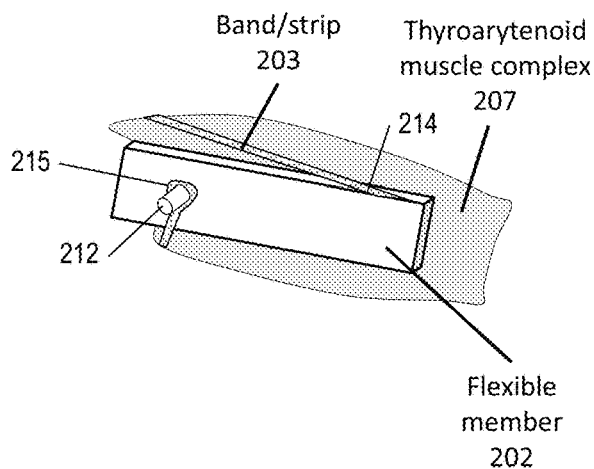

FIGS. 5A, 5B, and 5C illustrate methods of connecting the implant 201 with the thyroarytenoid muscle complex 207 in examples of the present disclosure. One or multiple bands 203 are attached to the flexible member 202. In FIG. 5A, the band 203 is wrapped around the thyroarytenoid muscle complex 207 with the distal end 215 of the band 203 attached to the flexible member 202. For example, the proximate end 214 of the band 203 is attached to the superior, inferior, lateral, or medial surface of the flexible member 202 while the distal end 215 of the band 203 is attached to the inferior, superior, lateral, or medial surface of the flexible member 202. In FIG. 5B, the band 203 is attached to the thyroarytenoid muscle complex 207 with sutures, clips, or hooks. For example, the proximate end 214 of the band 203 is attached to the superior, inferior, lateral, or medial surface of the flexible member 202 while the distal end 215 of the band 203 is attached to the thyroarytenoid muscle complex 207 with a suture 503. In FIG. 5C, the band 203 is wrapped around the thyroarytenoid muscle complex 207 and attached to the port connector 212 of the flexible member 202. For example, the proximate end 214 of the band 203 is attached to the superior, inferior, lateral, or medial surface of the flexible member 202 while a looped distal end 215 is hooked onto the port connector 212 of the flexible member 202.

Movement of the band(s) 203, after being interconnected to the thyroarytenoid muscle complex 207, causes traction force to the thyroarytenoid muscle complex 207, which causes the arytenoid cartilage 208 (FIG. 2) to rotate. This connection may also provide fixation of the implant preventing any relative movement in the paraglottic space.

Figure 6:
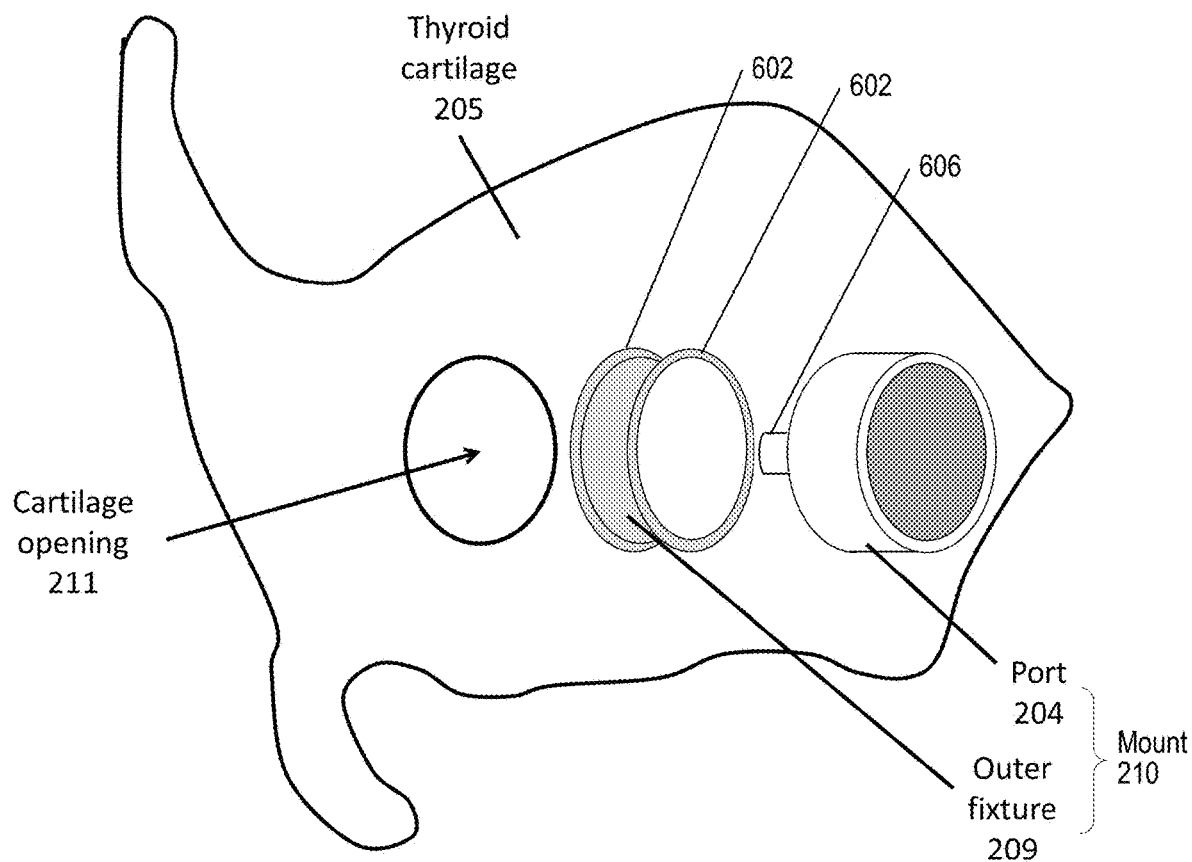
FIG. 6 illustrates the mount of FIG. 2 with an outer fixture to fit into a cartilage opening and a port to be placed into the outer fixture in examples of the present disclosure.

FIG. 6 illustrates the mount 210 with the outer fixture 209 to fit into the cartilage opening 211 and the port 204 to be placed into the outer fixture 209 in examples of the present disclosure. A surgeon or a medical machinery uses a surgical device to create the cartilage opening 211 on the patient's thyroid cartilage 205. The cartilage opening 211 may have a circular or rectangular shape. The surgical device may be, without limitations, a cutter, a drill, a saw, or a punch (e.g., a Kerrison punch). The surgical tool may be operated manually, electrically, mechanically, or magnetically.

After the surgeon or the medical machinery has delivered the implant into the patient's paraglottic space, the outer fixture 209 is placed into the cartilage opening 211. The outer fixture 209 may be made by using materials such as elastomer, silicone, polymer, synthetic material, ENT synthetic, porous polyethylene, ENT synthetic-PIFE, silicon elastomer, polyethylene, and polyurethane. The outer fixture 209 may be flexible so that it can be squeezed into the cartilage opening 211. The outer fixture 209 may have flanges 602 that cover the cartilage opening 211. The flanges 602 may prevent enlargement or progression of the crack or damage at the edge of the cartilage opening 211 during the surgery. The outer fixture 209 may have a rough outer side surface. As a result, when the outer fixture 209 is placed into the cartilage opening 211, the rough outer side surface may generate sufficient frictions to stabilize the outer fixture 209 from slipping or rotating in the cartilage opening 211. The outer fixture 209 may be further secured by nails or screws to the thyroid cartilage 205. Furthermore the outer fixture 209 can also function as an insertion plate, thus preventing the flexible member 202 from being damaged by cartilage window rough surface during implantation.

The port 204 is a device configured to maintain and deliver filler, therefore, filler may be added to or removed from the implant intraoperatively or postoperatively. The port 204 includes least one chamber with a septum 604 and an implant connector 606 that mates with the port connector 212 of the flexible member 202 (FIG. 2) for adding/extracting fillers to/from the flexible member 202. For example, the implant connector 606 of the port 204 has internal threads that screw onto external threads on the port connector 212 of the expandable member 202.

Figure 7:
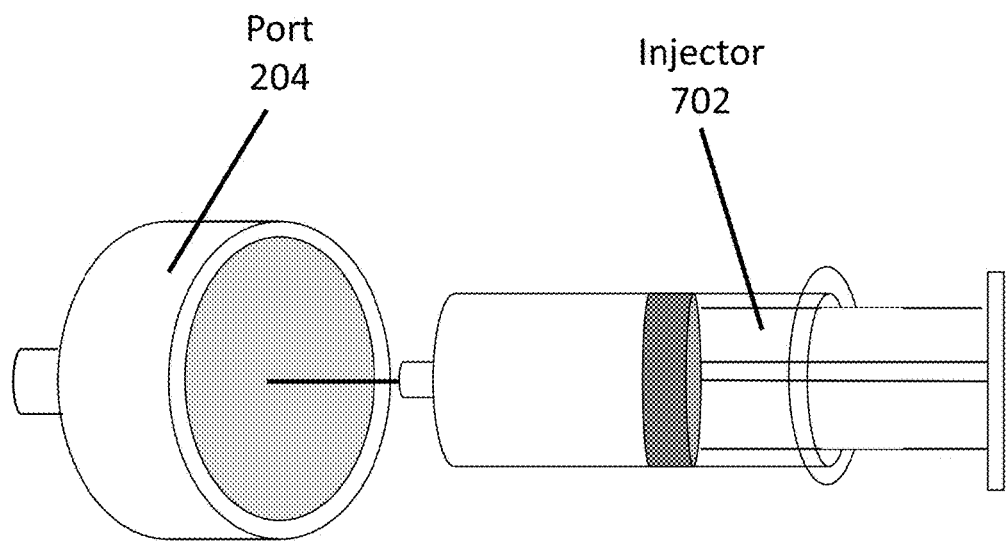
FIG. 7 illustrates using a delivering device to inject a filler into the port of FIG. 6 in examples of the present disclosure.

FIG. 7 illustrates diagram of using an injector 702 to deliver filler into the port 204 in examples of the present disclosure. The port 204 acts as a delivery mechanism to add filler to, or extract filler from, the expandable member 202 (FIG. 2). The port 204 may also act as a valve to maintain the amount of filler in the flexible member 202. The injector 702 may be used to add or extract filler via the septum 604. Once the injector 702 completes the adding or extracting actions, the septum 604 may automatically seal itself off, thereby maintaining the amount of filler in the semi-closed delivery system.

Figure 8A:
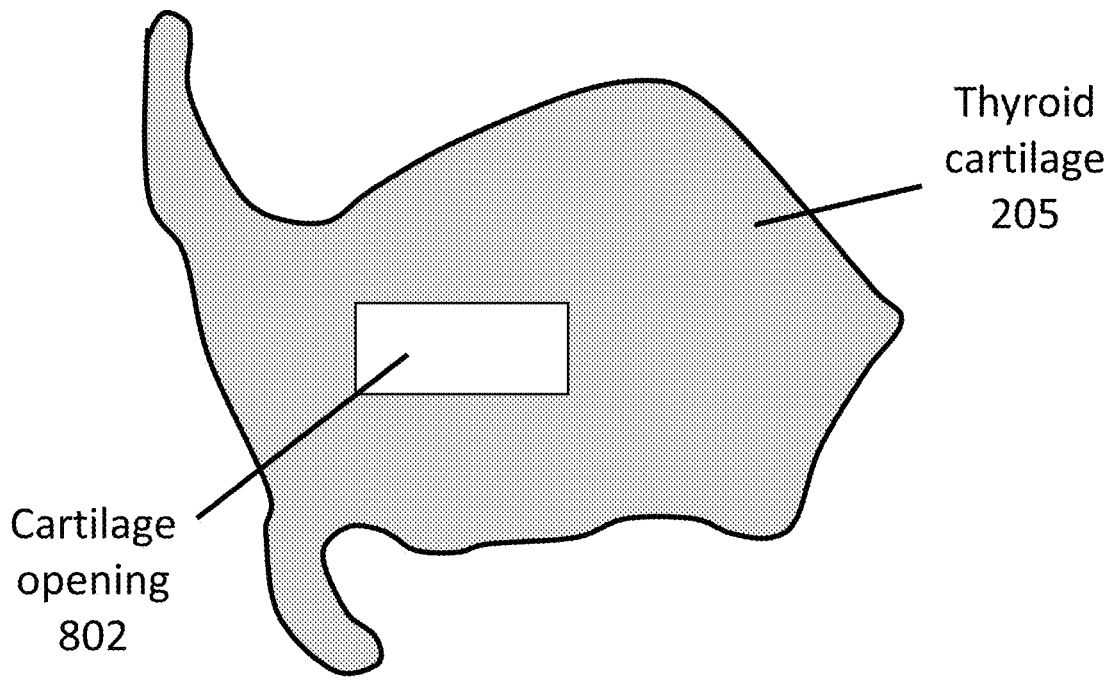
FIGS. 8A and 8B illustrate a mount with an outer fixture and a fixture plate to fit into a cartilage opening in examples of the present disclosure.
Figure 8B:
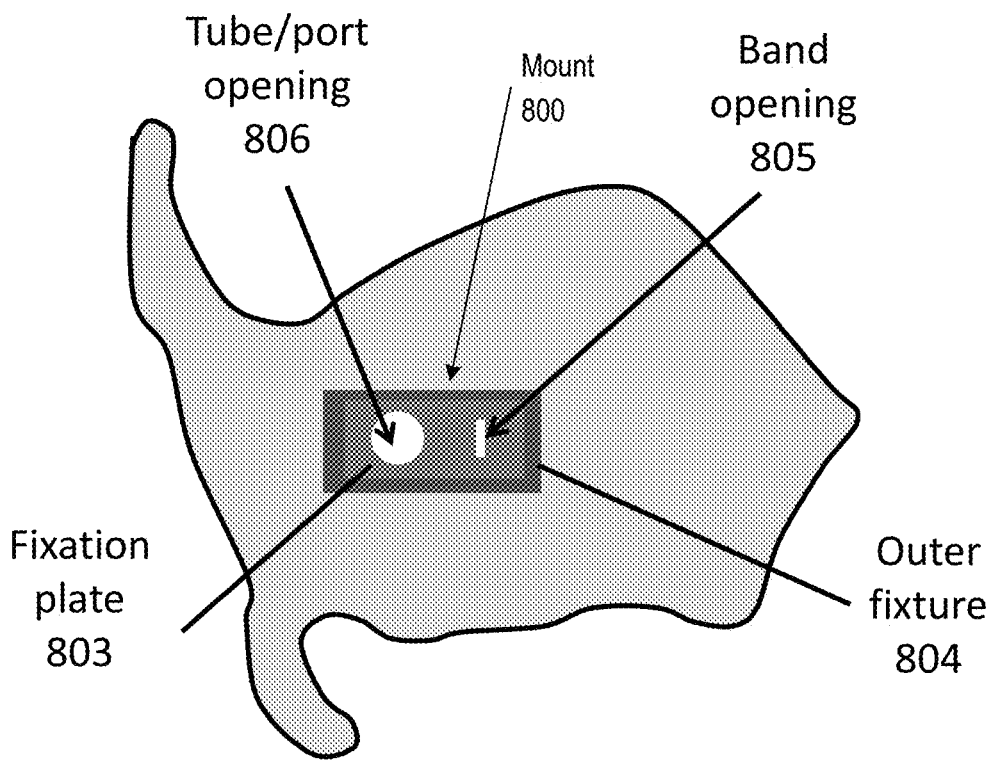

FIGS. 8A and 8B illustrate a mount 800 to fit into a cartilage opening 802 to fix an implant, such as the implant 201 (FIG. 2) or 901 (FIG. 9), in examples of the present disclosure. In FIG. 8A, a surgeon or a medical machinery uses a surgical device to create the cartilage opening 802 on the patient's thyroid cartilage 205. The cartilage opening 802 may have a rectangular or circular shape. The surgical device may be, without limitations, a cutter, a drill, a saw, or a punch (e.g., a Kerrison punch). The surgical tool may be operated manually, electrically, mechanically, or magnetically.

In FIG. 8B, after the surgeon or the medical machinery has delivered the implant into a patient's paraglottic space, the mount 800 with an outer fixture 804 and a fixation plate 803 are placed into the cartilage opening 802. The outer fixture 804 may be made by using materials such as elastomer, silicone, polymer, synthetic material, ENT synthetic, porous polyethylene, ENT synthetic-PIFE, silicon elastomer, polyethylene, and polyurethane. The outer fixture 804 may be flexible, so that it can be squeezed into the cartilage opening. The outer fixture 804 may have flanges that cover the cartilage opening 802. The flanges may be used to prevent enlargement or progression of the crack or damage at the edge of the cartilage opening 802 during the surgery and also prevent the implant from being damaged by the rough or sharp edges on the cartilage window during implantation.

After the outer fixture 804 is placed into the cartilage opening 802, a fixation plate 803 may be placed in the outer fixture 804. The fixation plate 803 may be made by using materials such as elastomer, silicone, polymer, synthetic material, ENT synthetic, porous polyethylene, ENT synthetic-PIFE, silicon elastomer, polyethylene, and polyurethane. The fixation plate 803 may be flexible so that it can be squeezed into the outer fixture 804. The fixation plate 803 may include a catheter/port opening 806 and a band opening 805. A catheter from the implant or an implant connector of a port (e.g., the implant connector 606 of the port 204) may go through the catheter/port opening 806 while the band 203 may go through the band opening 805 to be fixed with the fixation plate 803.

Figure 9:
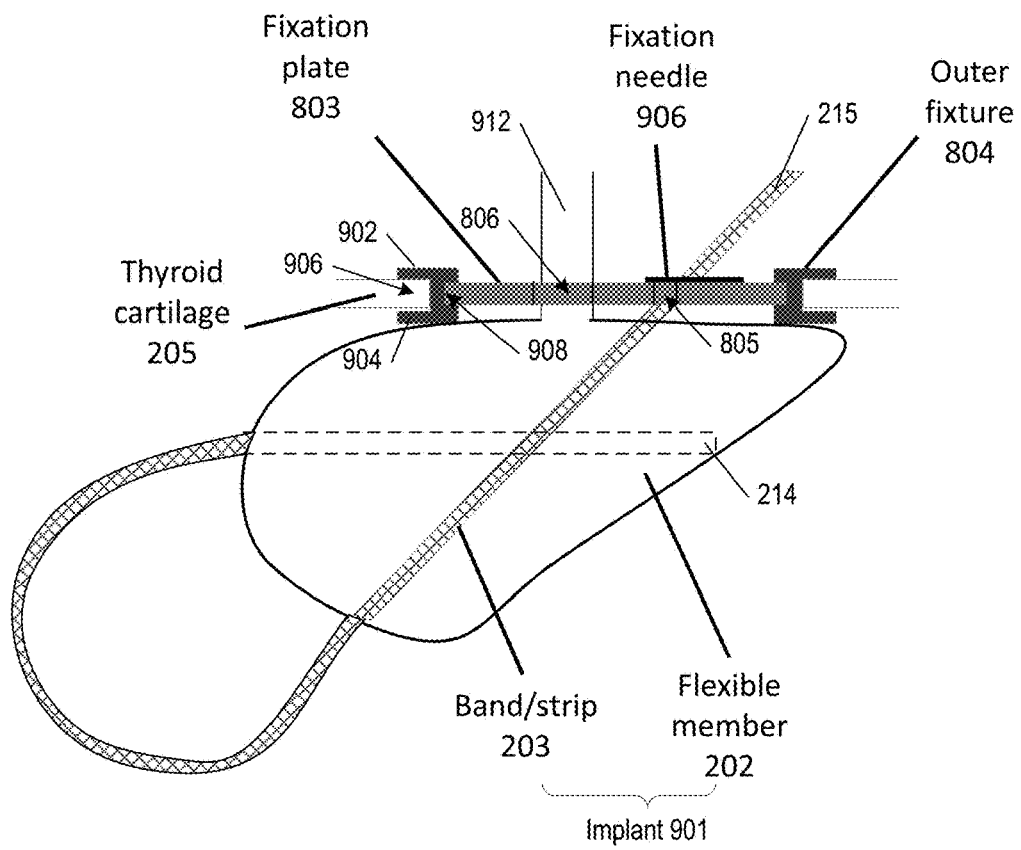
FIG. 9 illustrates the mount of FIGS. 8A and 8B fixing an implant in the paraglottic space in examples of the present disclosure.

FIG. 9 illustrates a bottom view of the mount 800 to fix an implant 901 in the paraglottic space in examples of the present disclosure. The implant 901 is similar to implant 201 but the expandable member 202 includes a catheter 912 instead of the port connector 212. The outer fixture 804 includes flanges 902 and 904 that form outer groove 906 and inner groove 908. The outer groove 906 is used to fix the outer fixture 804 inside the cartilage opening 802 of the thyroid cartilage 205. The fixation plate 803 is fixed at the inner groove 908 of the outer fixture 804. The catheter 912 on the lateral side of the flexible member 202 extends through the catheter/port opening 806 to connect with the implant connector 606 of the port 204. In other examples where the implant 201 is used with the mount 800, the port connector 212 on the lateral side of the flexible member 202 extends through the catheter/port opening 806 to connect with the implant connector 606 of the port 204. The band 203 is wrapped around the thyroarytenoid muscle complex 207, and the distal end 215 of the band 203 goes through the band opening 805 of the fixation plate 803 and becomes fixed using a fixation needle or pin 906.

Figure 10:
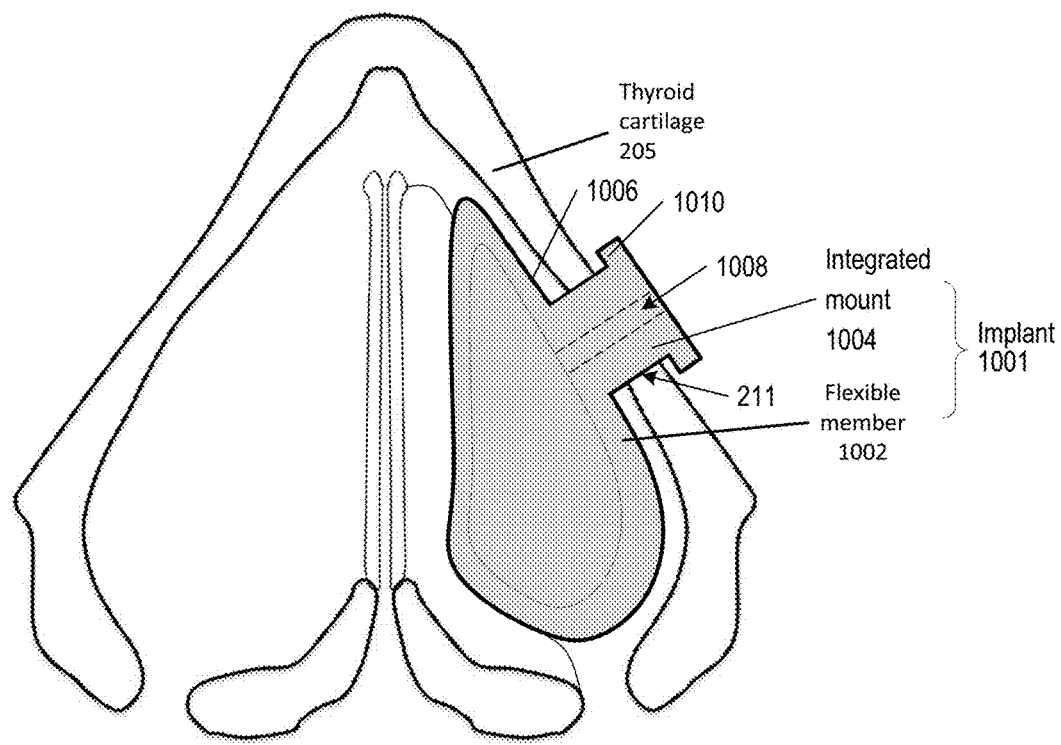
FIG. 10 illustrates an implant including a flexible member and a mount integrated with the flexible member in examples of the present disclosure.

FIG. 10 illustrates an implant 1001 including an expandable member 1002 and a mount 1004 integrated with the expandable member 1002 in examples of the present disclosure. Flexile member 1002 is a variation of the expandable member 202 where the band 203 has been omitted for clarity's sake. The integrated mount 1004 is a flanged tubular portion that extends from a lateral side 1006 of the expandable member 1002. The integrated mount 1004 defines a channel 1008 to be connected to a port connector or catheter to be connected to a port. The portion of the integrated mount 1004 between a flange 1010 at the end of the integrated mount 1004 and the lateral side 1006 of the expandable member 1002 defines a groove that fixes the implant 1000 in the opening 211 of the thyroid cartilage 205. The integrated mount 1004 may be made by using materials such as elastomer, silicone, polymer, synthetic material, ENT synthetic, porous polyethylene, ENT synthetic-PIFE, silicon elastomer, polyethylene, and polyurethane. The integrated mount 1004 may be flexible so that it can be squeezed into the opening 211 of the thyroid cartilage 205.

Figure 11:
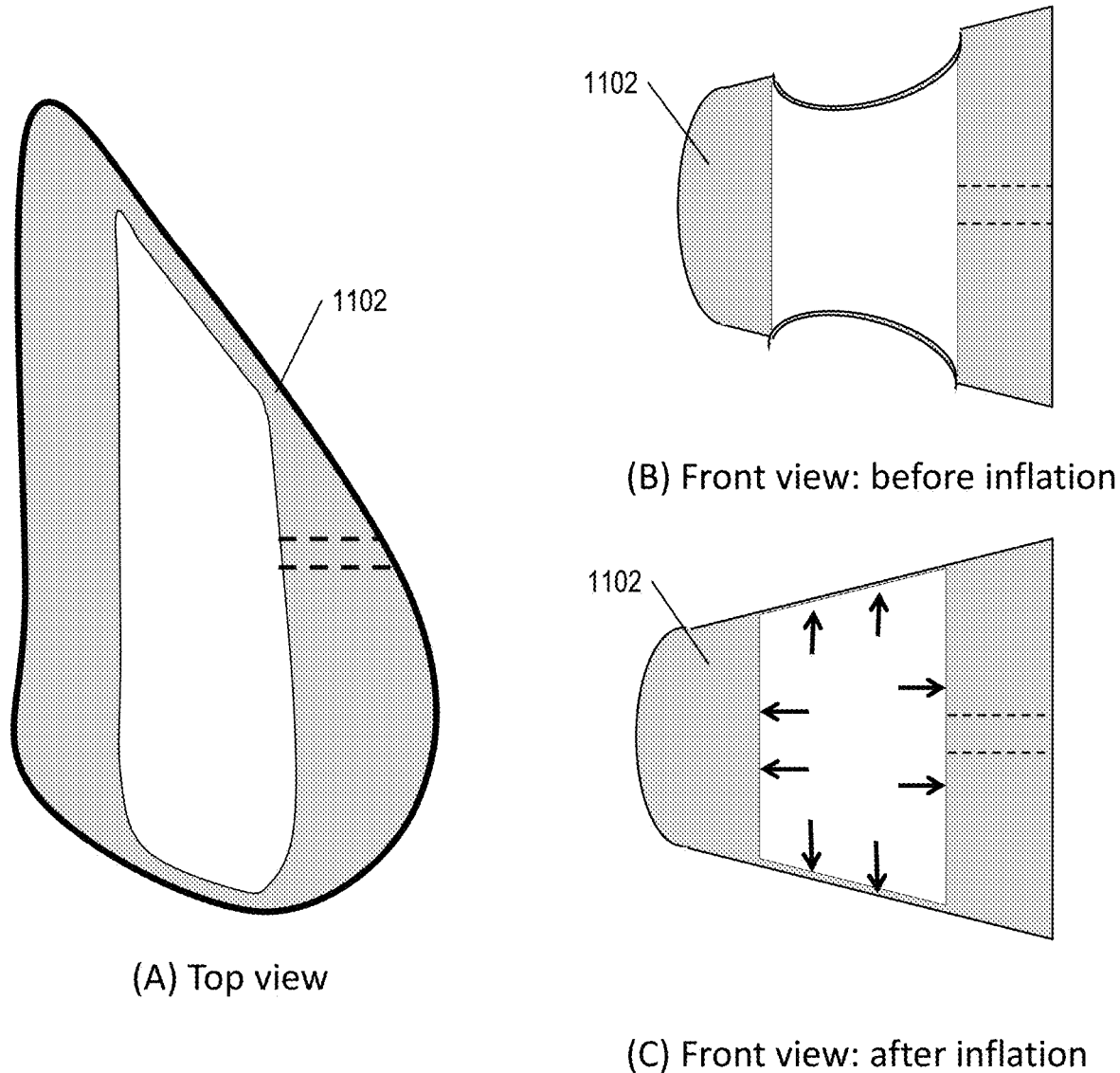
FIG. 11 illustrates inflating an implant in examples of the present disclosure.

FIG. 11 illustrates inflating an implant with an expandable member 1102 in examples of the present disclosure. The expandable member 1102 is a variation of the expandable member 202 where the band 203 has been omitted for clarity's sake. FIG. 11A shows a top view of the expandable member 1102, FIG. 11B shows a front view of the expandable member 1102 before inflation, and FIG. 11C shows a front view of the expandable member 1102 after inflation. Boundary of the expandable member may have different properties to control the inflation of the expandable member in a desired direction, volume, pressure, and/or force. These properties may include but not limited to the thickness, density, stiffness, and elasticity of the boundary of the expandable member 1102. For example, as shown in FIG. 11B, the expandable member 1102 is thicker at medial and lateral sides, and thinner at top and bottom sides. The expandable member 1102 is narrower at the middle section. As the expandable member 1102 is inflated, FIG. 11C shows the expandable member 1102 expands laterally greater than vertically and longitudinally.

Referring back to FIGS. 2A and 2B, in some examples of the present disclosure, the implant 201 has a main body 202 that is a mechanical, electrical, magnetic, or piezoelectric actuator. The actuator 202 can elongate to pull on the band 203, which in turn pulls on the thyroarytenoid muscle complex 207, which in turn rotates the arytenoids cartilage 208 to medialize and tighten the vocal cord 206.

In other examples of the present disclosure, the implant 201 has a main body 202 of a fixed size. The implant 201 is selected from implants having main bodies of different sizes to match a patient's the paraglottic space. Alternatively material is removed from the main body 202 to match the patient's paraglottic space. The length of band 203 between its attachment points determines the pull on the thyroarytenoid muscle complex 207, which in turn determines the rotation of the arytenoids cartilage 208 to medialize and tighten the vocal cord 206.

The actuator 202 or the fixed size main body 202 has a mount connector 212 instead of the port connector 212 to be fixed to the mount 210. The mount 210 is a closed piece with the implant connector 606 but without the port 204, or the port 204 is replaced with an inner fixture 204 inside the outer fixture 209. Alternatively the actuator 202 is fixed to the mount 800 (FIG. 8B) with an implant connector 806 instead of an implant connector/port opening 806.

Thus, apparatuses and methods for treating glottic insufficiency have been disclosed. The various embodiments described herein may employ a device or an apparatus for performing these methods. The apparatus may be specially constructed for specific required purposes, or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations. The various embodiments described herein may be practiced with other computer system configurations including hand-held devices, microprocessor systems, microprocessor-based or programmable consumer electronics, minicomputers, mainframe computers, and the like.

Although one or more embodiments of the present disclosure have been described in some detail for clarity of understanding, it will be apparent that certain changes and modifications may be made within the scope of the claims. Accordingly, the described embodiments are to be considered as illustrative and not restrictive, and the scope of the claims is not to be limited to details given herein, but may be modified within the scope and equivalents of the claims. In the claims, elements and/or steps do not imply any particular order of operation, unless explicitly stated in the claims.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure(s). In general, structures and functionality presented as separate components in exemplary configurations may be implemented as a combined structure or component. Similarly, structures and functionality presented as a single component may be implemented as separate components. These and other variations, modifications, additions, and improvements may fall within the scope of the appended claims(s).

What is claimed is:

1. An implant system for treating glottic insufficiency, comprising:
    an implant, comprising:
        a balloon with a port connector or a catheter; and
        a band comprising a proximate end attached to a portion of the balloon, wherein the portion of the balloon translates away from the port connector or the catheter when the balloon is inflated through the port connector or the catheter, and the balloon comprises medial and lateral sides that are thicker than top and bottom sides so the balloon expands laterally greater than vertically and longitudinally when the balloon is inflated.

2. The implant system of claim 1, wherein the balloon comprises a substantially triangular block shaped balloon.

3. The implant system of claim 2, wherein the substantially triangular block shaped balloon has a first lateral surface corresponding to an arytenoid cartilage, a second lateral surface corresponding to a vocal cord, and a third lateral surface corresponding to a thyroid cartilage.

4. The implant system of claim 3, wherein the port connector or the catheter protrudes from the third lateral surface.

5. The implant system of claim 4, wherein the proximate end of the band is attached to a superior surface, a lateral surface, an inferior surface, or a medial surface of the balloon.

6. The implant system of claim 5, further comprising:
    a mount, comprising:
        a fixture fit to a window opened in the thyroid cartilage; and
        a port in the fixture, the port comprising an implant connector capable of being secured to the port connector.

7. The implant system of claim 6, wherein the band comprises a looped distal end.

8. The implant system of claim 6, wherein the fixture comprises flanges.

9. The implant system of claim 6, wherein the port connector and the implant connector comprise threads to engage each other.

10. The implant system of claim 6, wherein the balloon comprises silicon and the band comprises a meshed textile integrated into a biocompatible material.

11. The implant system of claim 1, further comprising:
    a mount, comprising:
        an outer fixture fit to a window opened in the thyroid cartilage; and
        a fixation plate in the outer fixture, the fixation plate defining an opening to receive the port connector or the catheter.

12. The implant system of claim 11, wherein the fixation plate further defines another opening to receive a distal end of the band.

13. The implant system of claim 1, wherein the implant further comprises a mount integrated with the balloon to fix the implant to a window opened in the thyroid cartilage.

* * * * *